US012390347B2

(12) United States Patent
Hapstack et al.

(10) Patent No.: US 12,390,347 B2
(45) Date of Patent: *Aug. 19, 2025

(54) ANTERIOR LUMBAR INTERBODY FUSION DEVICE WITH BIDIRECTIONAL SCREWS

(71) Applicant: MiRus LLC, Marietta, GA (US)

(72) Inventors: Chris Hapstack, Marietta, GA (US); Jorge Isaza, Baton Rouge, LA (US)

(73) Assignee: MiRus LLC, Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,946

(22) Filed: Feb. 19, 2024

(65) Prior Publication Data

US 2024/0268973 A1 Aug. 15, 2024

Related U.S. Application Data

(63) Continuation of application No. 17/179,056, filed on Feb. 18, 2021, now Pat. No. 11,957,600.

(60) Provisional application No. 62/978,060, filed on Feb. 18, 2020.

(51) Int. Cl.
*A61F 2/44* (2006.01)
*A61F 2/30* (2006.01)

(52) U.S. Cl.
CPC .... *A61F 2/447* (2013.01); *A61F 2002/30774* (2013.01); *A61F 2002/30784* (2013.01); *A61F 2002/30838* (2013.01); *A61F 2002/30841* (2013.01); *A61F 2310/00023* (2013.01); *A61F 2310/00029* (2013.01); *A61F 2310/00101* (2013.01)

(58) Field of Classification Search
CPC .......... A61F 2/44; A61F 2/442; A61F 2/4455; A61F 2/446; A61F 2/4465; A61F 2/447; A61F 2002/30578; A61F 2002/30787
See application file for complete search history.

(56) References Cited

U.S. PATENT DOCUMENTS

| | | | |
|---|---|---|---|
| 7,488,444 B2 | 2/2009 | Furst et al. | |
| 8,740,983 B1* | 6/2014 | Arnold | A61F 2/4611 623/17.16 |
| 9,381,093 B1* | 7/2016 | Morris | A61B 17/8042 |
| 9,655,742 B2* | 5/2017 | Marnay | A61F 2/44 |
| 9,662,226 B2 | 5/2017 | Wickham | |
| 9,687,358 B2 | 6/2017 | Bertele et al. | |
| 9,848,995 B2 | 12/2017 | Ulrich, Jr. | |

(Continued)

OTHER PUBLICATIONS

Pavon, J. et al., "Titanium scaffolds with multi-scale porosity obtained by controlled chemical and electrochemical treatments of porous solids from PM space holder technique", 10th World Biomaterials Congress Event Abstract (2016).

*Primary Examiner* — Eric S Gibson
(74) *Attorney, Agent, or Firm* — UB Greensfelder LLP (57) ABSTRACT

Various implementations include an implant. The implant includes a body defining a central opening. The body has a first surface and a second surface spaced apart and opposite from the first surface. The second surface at least partially defines the central opening. The first surface defines a plurality of openings including a first opening and a second opening. Each of the openings extends along an axis from the first surface to the second surface. The first opening and the second opening at least partially overlap at the first surface, and the axis of the first opening is transverse to the axis of the second opening.

30 Claims, 9 Drawing Sheets

(56) References Cited

U.S. PATENT DOCUMENTS

| | | | |
|---|---|---|---|
| 9,848,996 B2* | 12/2017 | Faulhaber | A61F 2/4455 |
| 9,855,150 B2* | 1/2018 | Altarac | A61F 2/4455 |
| 10,687,956 B2* | 6/2020 | Ullrich, Jr. | A61F 2/4465 |
| 11,116,644 B2* | 9/2021 | Marrocco | A61F 2/4455 |
| 11,957,600 B2* | 4/2024 | Hapstack | A61F 2/4455 |
| 2002/0153348 A1 | 10/2002 | Say et al. | |
| 2003/0040798 A1 | 2/2003 | Michelson | |
| 2006/0074490 A1 | 4/2006 | Sweeney | |
| 2011/0035009 A1 | 2/2011 | Sweeney | |
| 2011/0082551 A1 | 4/2011 | Kraus | |
| 2011/0224796 A1 | 9/2011 | Weiland et al. | |
| 2011/0301714 A1* | 12/2011 | Theofilos | A61F 2/4465 623/17.16 |
| 2012/0172991 A1 | 7/2012 | Bertele et al. | |
| 2012/0277870 A1* | 11/2012 | Wolters | A61F 2/447 623/17.16 |
| 2012/0303127 A1 | 11/2012 | Ulrich, Jr. et al. | |
| 2012/0316653 A1 | 12/2012 | Ulrich, Jr. et al. | |
| 2013/0116793 A1 | 5/2013 | Kloss | |
| 2013/0226300 A1* | 8/2013 | Chataigner | A61F 2/4455 623/17.16 |
| 2014/0012380 A1* | 1/2014 | Laurence | A61F 2/4465 623/17.16 |
| 2014/0100662 A1 | 4/2014 | Patterson et al. | |
| 2014/0277491 A1 | 9/2014 | Fang et al. | |
| 2014/0336771 A1* | 11/2014 | Zambiasi | A61F 2/4455 623/17.16 |
| 2015/0018959 A1 | 1/2015 | Tornier et al. | |
| 2015/0328005 A1* | 11/2015 | Padovani | A61F 2/442 623/17.13 |
| 2015/0359639 A1* | 12/2015 | Ullrich, Jr. | A61F 2/4455 623/17.11 |
| 2016/0235448 A1* | 8/2016 | Seex | A61B 17/808 |
| 2016/0270920 A1 | 9/2016 | Dawson et al. | |
| 2016/0331543 A1 | 11/2016 | Butler et al. | |
| 2017/0156880 A1 | 6/2017 | Halverson et al. | |
| 2017/0189204 A1* | 7/2017 | Riemhofer | A61B 17/8877 |
| 2018/0071113 A1 | 3/2018 | Melkent et al. | |
| 2018/0318099 A1* | 11/2018 | Altarac | A61B 17/8042 |
| 2018/0318100 A1* | 11/2018 | Altarac | A61F 2/4455 |
| 2019/0254840 A1 | 8/2019 | Gray et al. | |
| 2020/0054461 A1* | 2/2020 | Marrocco | A61F 2/4455 |
| 2020/0246162 A1* | 8/2020 | Schultz | A61F 2/4611 |
| 2021/0077268 A1* | 3/2021 | Struck | A61F 2/447 |
| 2021/0154022 A1* | 5/2021 | Walsh | A61F 2/447 |
| 2021/0251769 A1* | 8/2021 | Hapstack | A61F 2/447 |
| 2022/0233329 A1* | 7/2022 | Marrocco | A61F 2/4455 |
| 2024/0268973 A1* | 8/2024 | Hapstack | A61F 2/447 |

\* cited by examiner

ANTERIOR LUMBAR INTERBODY FUSION DEVICE WITH BIDIRECTIONAL SCREWS

CROSS-REFERENCE TO RELATED APPLICATIONS

This application is a continuation of U.S. Ser. No. 17/179,056 filed Feb. 18, 2021, which in turn claims the benefit of U.S. Provisional Patent Application No. 62/978,060, filed Feb. 18, 2020, the contents of which are incorporated herein by reference in their entirety.

BACKGROUND

An interbody device is a prosthesis used during spinal surgery. An interbody device is inserted into the space between spinal disks to provide stability. For example, an interbody device can be introduced between vertebrae of a patient's spine (i.e., in the disk space between adjacent vertebrae) for fixation with bone to immobilize the joint as part of a surgical treatment. Interbody devices are fastened with anchors and often have a plurality of single openings for insertion of each anchor. The single openings provide a predetermined location in the spinal column for each anchor to be inserted during an operation. However, due to differences in patients' spines and existing medical hardware, the specific anchor locations of current interbody devices may be unsuitable in some cases.

Thus, a need exists for an implantable interbody device that provides for versatility of anchor insertion locations.

SUMMARY

Various implementations include an implant. The implant includes a body defining a central opening, the body has a first surface and a second surface spaced apart and opposite from the first surface. The second surface at least partially defines the central opening. The first surface defines a plurality of openings including a first opening and a second opening. Each of the openings extends along an axis from the first surface to the second surface. The first opening and the second opening at least partially overlap at the first surface, and the axis of the first opening is transverse to the axis of the second opening.

In some implementations, the plurality of openings further includes a third opening, a fourth opening, a fifth opening and a sixth opening. The third opening and the fourth opening at least partially overlap at the first surface, and the axis of the third opening is transverse to the axis of the fourth opening. The fifth opening and the sixth opening at least partially overlap at the first surface, and the axis of the fifth opening is transverse to the axis of the sixth opening.

In some implementations, the first surface of the body further includes an alignment axis. An intersection point of the axis of the first opening with the first surface and an intersection point of the axis of the second opening with the first surface are equally spaced on opposite sides of the alignment axis from each other. An intersection point of the axis of the third opening with the first surface and an intersection point of the axis of the fourth opening with the first surface are equally spaced on opposite sides of the alignment axis from each other. An intersection point of the axis of the fifth opening with the first surface and an intersection point of the axis of the sixth opening with the first surface are equally spaced on opposite sides of the alignment axis from each other.

In some implementations, the first opening and the second opening are configured such that a first anchor is disposable within the first opening and a second anchor is disposable within the second opening simultaneously.

In some implementations, the axis of the first opening and the axis of the second opening define an anchor plane that is perpendicular to the alignment axis. The axis of the first opening is disposed at a first angle from 30 degrees to 60 degrees relative to the second surface of the body. The axis of the second opening is disposed at a second angle from 30 degrees to 60 degrees relative to the second surface of the body.

In some implementations, the first angle is 45 degrees and second angle is 45 degrees.

In some implementations, a projection of the axis of the third opening onto the anchor plane is disposed at a third primary angle from 15 degrees to 60 degrees relative to the second surface of the body. A projection of the axis of the fourth opening onto the anchor plane is disposed at a fourth primary angle from 15 degrees to 60 degrees relative to the second surface of the body. A projection of the axis of the fifth opening onto the anchor plane is disposed at a fifth primary angle from 15 degrees to 60 degrees relative to the second surface of the body. A projection of the axis of the sixth opening onto the anchor plane is disposed at a sixth primary angle from 15 degrees to 60 degrees relative to the second surface of the body.

In some implementations, the third primary angle is 30 degrees, fourth primary angle is 30 degrees, fifth primary angle is 30 degrees, and sixth primary angle is 30 degrees.

In some implementations, the axis of the third opening intersects the anchor plane at a third secondary angle of 30 degrees or less, and wherein the axis of the fourth opening intersects the anchor plane at a fourth secondary angle of 30 degrees or less. The axis of the fifth opening intersects the anchor plane at a fifth secondary angle of 30 degrees or less. The axis of the sixth opening intersects the anchor plane at a sixth secondary angle of 30 degrees or less.

In some implementations, the third secondary angle is 15 degrees, the fourth secondary angle is 15 degrees, the fifth secondary angle is 15 degrees, and the sixth secondary angle is 15 degrees.

In some implementations, the axes of the third opening and the fourth opening intersect the anchor plane at a first point that is closer to the second surface than to the first surface. The axes of the fifth opening and the sixth opening intersect the anchor plane at a second point that is closer to the second surface than to the first surface.

In some implementations, the plurality of openings further includes a seventh opening, an eighth opening. The seventh opening and the eighth opening at least partially overlap at the first surface, and the axis of the seventh opening is transverse to the axis of the eighth opening.

In some implementations, the seventh opening and the eighth opening are configured such that a first anchor is disposable within the seventh opening and a second anchor is disposable within the eighth opening simultaneously.

In some implementations, the axis of the seventh opening and the axis of the eighth opening extend parallel to the anchor plane, wherein the axis of the seventh opening is disposed at a 45 degree angle relative to the second surface of the body. The axis of the eighth opening is disposed at a 45 degree angle relative to the second surface of the body and at a 90 degree angle relative to the axis of the seventh opening.

In some implementations, the implant includes an anti-backout device coupled to the first surface of the body, wherein the anti-backout device is positionable to cover a portion of at least the first opening and the second opening.

In some implementations, the implant includes an interbody device.

In some implementations, the body includes a molybdenum-rhenium (MoRe) alloy.

In some implementations, the MoRe alloy is Mo47.5Re.

In some implementations, the body includes at least 40 weight percent rhenium (Re).

In some implementations, the body includes a titanium-molybdenum (TiMo) alloy.

In some implementations, the body comprises a cobalt-chromium (CoCr) alloy.

In some implementations, the body comprises a titanium (Ti) alloy.

In some implementations, the body comprises polyether ether ketone ("PEEK").

In some implementations, the body defines a plurality of micro-apertures having an average size between about 2 to about 10 micrometers (μm) and a plurality of macro-apertures having an average size between about 300 to about 800 micrometers (μm).

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

The devices, systems, and methods disclosed herein provide for an implantable interbody device that can be implanted between adjacent vertebrae in the lumbar region of the spine to promote fusion of the vertebrae. The implant includes a plurality of anchor openings at different angles to allow a surgent to determine the optimal anchor location in each case. By partially overlapping the anchor openings of the implant, the implant is able to include more anchor openings to provide more anchoring options.

Various implementations include an implant. The implant includes a body defining a central opening. The body has a first surface and a second surface spaced apart and opposite from the first surface. The second surface at least partially defines the central opening. The first surface defines a plurality of openings including a first opening and a second opening. Each of the openings extends along an axis from the first surface to the second surface. The first opening and the second opening at least partially overlap at the first surface, and the axis of the first opening is transverse to the axis of the second opening.

FIGS. 1-6 show an implant 100 according to one implementation. The implant 100 includes a body 110, a plurality of anchors 199, a first anti-backout device, and a second anti-backout device. The body 110 is a toroidal shape that defines a central opening 112 to promote bone growth. The body 110 has an inner surface 116 defining the central opening 112, an outer surface 114 opposite and spaced apart from the inner surface 116, a superior surface 120 extending between the inner surface 116 and the outer surface 114, and an inferior surface 122 opposite and spaced apart from the superior surface 120. A portion of the outer surface 114 includes a first surface 124, and a portion of the inner surface 116 includes a second surface 126 spaced apart and opposite from the first surface 124.

The first surface 124 and the second surface 126 each have a width as measured between the superior surface 120 and the inferior surface 122. The first surface 124 has a width that is greater than the width of the second surface 126 such that the superior surface 120 and the inferior surface 122 form a lordosis angle relative to each other that corresponds with a lordosis angle of the adjacent vertebrae between which the device will be implanted. The lordosis angle of the implant 100 shown in FIGS. 1-9 is 12 degrees, but in other implementations, the lordosis angle is 5 degrees, 20 degrees, or any other angle from 0 degrees to 30 degrees.

Figure 1:
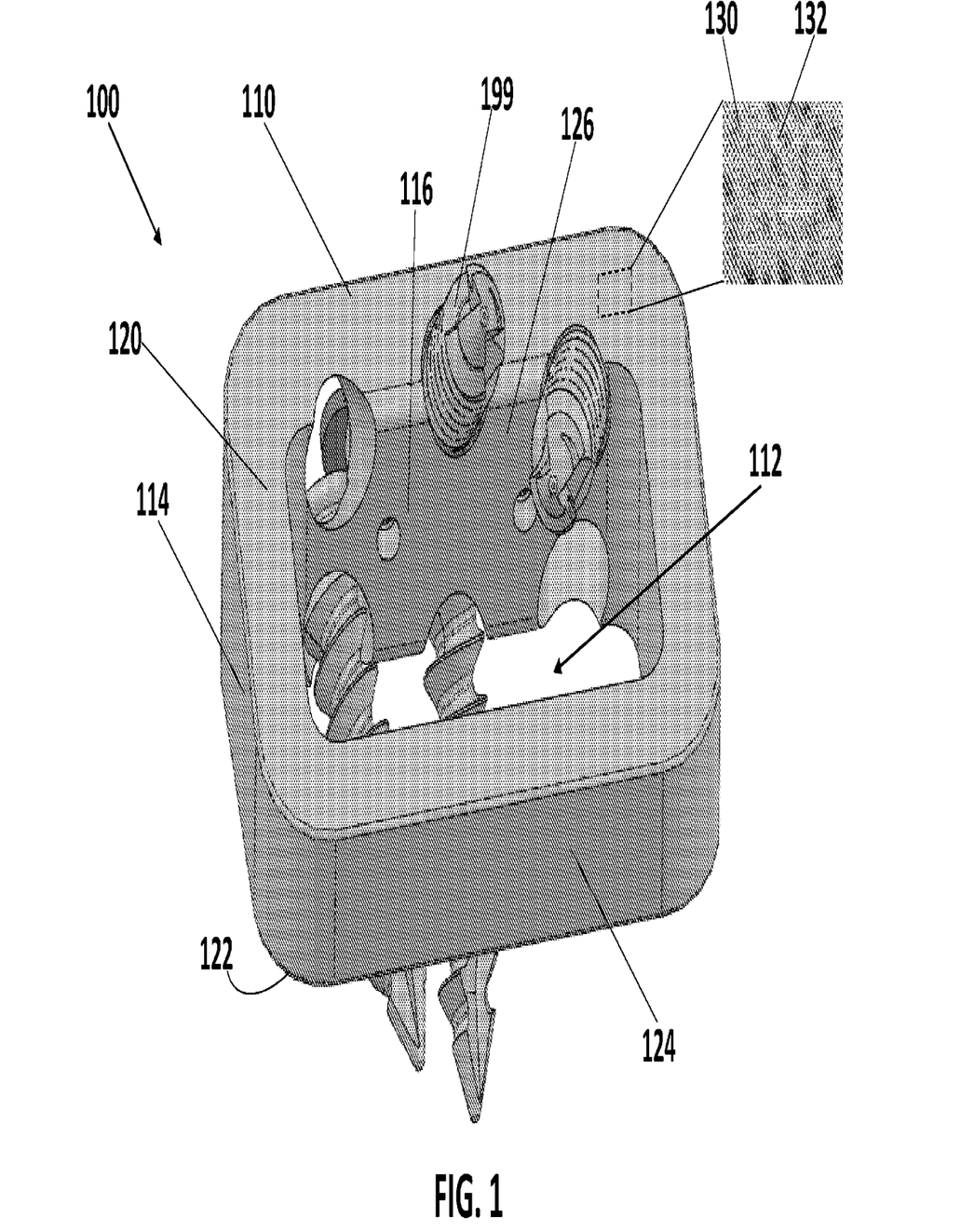
FIG. 1 is a rear perspective view of the implant.

The superior surface 120 and inferior surface 122 of the body 110 shown in FIG. 1 define a plurality of micro-apertures 130 and macro-apertures to allow bone growth into the body 110. Example micro-apertures 130 are shown in detail in FIG. 1. The micro-apertures 130 are configured to promote on-growth of bone. For example, micro-apertures 130 have an average size of about 6 micrometers (μm). The micro-apertures 130 create channels through which bone can grow to facilitate spinal fusion. It should be understood that material (e.g., bone fusion material), cells, tissue, and/or fluid can flow through the micro-apertures 130, which facilitates on-growth of bone. In some implementations, the micro-apertures 130 are homogeneous. In other implementations, the micro-apertures 130 have varying sizes and/or shapes (with the average size falling between about 2 μm to about 10 μm). The micro-apertures 130 can optionally be patterned and/or randomly located on the superior surface 120 and inferior surface 122 of the body 110.

The superior surface 120 and inferior surface 122 of the body 110 also include a plurality of macro-apertures 132. Example macro-apertures 132 are shown in detail in FIG. 1. The macro-apertures 132 are configured to promote through-growth of bone. For example, macroapertures 112B have an average size of about 500 μm. The macro-apertures 132 create channels through which bone can grow to facilitate spinal fusion. It should be understood that material (e.g., bone fusion material), cells, tissue, and/or fluid can flow through the macro-apertures 132, which facilitates through-growth of bone. In some implementations, the macro-apertures 132 are homogeneous. In other implementations, the macro-apertures 132 have varying sizes and/or shapes (with the average size falling between about 300 μm to about 800 μm). The macro-apertures 132 can optionally be patterned and/or randomly located on the superior surface 120 and inferior surface 122 of the body 110.

In some implementations, the micro- and/or macro-apertures 130, 132 can be provided such that the implant 100 has a stiffness equal to or greater than cancellous bone. Alternatively or additionally, the interbody device 100 can optionally have a composite porosity of 75-85% with 300-800 μm pores and 2-10% porosity with 10-50 μm pores. For comparison, cancellous bone has 75-85% porosity with 300-600 μm pores and cortical bone has 5-10% porosity with 10-50 82 m pores. By including micro- and macro-apertures 132, 112B, highly porous contacting superior surfaces 120 and inferior surfaces 122 are provided. Such porous superior surfaces 120 and inferior surfaces 122 facilitate spinal fusion. Porosity is achieved by providing a plurality of apertures (i.e., both micro- and macro-apertures 130, 132) that connect the superior surface 120 and inferior surface 122. As described below, the micro- and macro-apertures 130, 132 can be manufactured using a chemical etching process.

The body 110 includes Mo47.5Re molybdenum-rhenium (MoRe) alloy. But in some implementations, the body 110 includes any molybdenum-rhenium (MoRe) alloy. In other implementations, the body 110 includes any material that includes 40 weight percent rhenium (Re). In other implementations, the body includes polyether ether ketone ("PEEK"), but in other implementations, the body can include any other polymer suitable. In other implementations, the body includes material that includes titanium-molybdenum (TiMo) alloy, cobalt-chromium (CoCr) alloy, titanium (Ti) alloy, or any other material suitable for implantation in a human body. The body 110, 210 shown in FIGS. 1-9 is sized to be disposed between adjacent vertebrae of the lumbar region of the spine, but in other implementations, the body is sized to be disposed between adjacent vertebrae of the cervical spine.

FIGS. 1-5 show the first surface 124 defining a first opening 140, a second opening 144, a third opening 150, a fourth opening 154, a fifth opening, and a sixth opening. Each of the openings extends along a separate axis from the first surface 124 to the second surface 126. Each of the openings is sized to receive a screw 199 and is countersunk to receive a screw head.

Each of the openings partially overlap with another of the openings at the first surface 124. For example, in FIGS. 1-5, the first opening 140 and the second opening 144 at least partially overlap at the first surface 124, the third opening 150 and the fourth opening 154 at least partially overlap at the first surface 124, and the fifth opening 160 and the sixth opening 164 at least partially overlap at the first surface 124.

The first surface 124 of the body 110 includes an alignment axis 180 that extends longitudinally along the first surface 124 and runs centrally between sets of overlapping openings on the first surface 124. Specifically, an intersection point of the axis 142 of the first opening 140 with the first surface 124 and an intersection point of the axis 146 of the second opening 144 with the first surface 124 are equally spaced on opposite sides of the alignment axis 180 from each other. Similarly, an intersection point of the axis 152 of the third opening 150 with the first surface 124 and an intersection point of the axis 156 of the fourth opening 154 with the first surface are equally spaced on opposite sides of the alignment axis 180 from each other. Furthermore, an intersection point of the axis 162 of the fifth opening 160 with the first surface 124 and an intersection point of the axis 166 of the sixth opening 164 with the first surface 124 are equally spaced on opposite sides of the alignment axis 180 from each other.

Although the implementations shown in FIGS. 1-5 show that the intersection point of the axis 142 of the first opening 140 with the first surface 124 and the intersection point of the axis 146 of the second opening 144 with the first surface 124 are equally spaced on opposite sides of the alignment axis 180 from each other, in other implementations, the first opening 140 is a different distance from the alignment axis 180 than the second opening 144.

Although the implementations shown in FIGS. 1-5 show that the intersection point of the axis 152 of the third opening 150 with the first surface 124 and the intersection point of the axis 156 of the fourth opening 154 with the first surface 124 are equally spaced on opposite sides of the alignment axis 180 from each other, in other implementations, the third opening 150 is a different distance from the alignment axis than the fourth opening 154.

Although the implementations shown in FIGS. 1-5 show that the intersection point of the axis 162 of the fifth opening 160 with the first surface 124 and the intersection point of the axis 166 of the sixth opening 164 with the first surface 124 are equally spaced on opposite sides of the alignment axis 180 from each other, in other implementations, the fifth opening 160 is a different distance from the alignment axis 180 than the sixth opening 164.

The axis of each opening 142, 144, 146, 148, 150, 152 is angled relative to the second surface 126 to provide a surgeon with a plurality of angles through which the anchor 199 can be disposed. The axis 142 of the first opening 140 extends from the first surface 124 to the second surface 126 in a superior direction, and the axis 146 of the second opening 144 extends between the first surface 124 and the second surface 126 in an inferior direction. The axes 142, 146 of the first opening 140 and the second opening 144 define an anchor plane 182 that is perpendicular to the alignment axis 180.

The axis 142 of the first opening 140 is disposed at a first primary angle of 45 degrees relative to the second surface 126 of the body 110. The axis 146 of the second opening 144 is disposed at a second primary angle of 45 degrees relative to the second surface 126 of the body 110 and transverse to the axis 142 of the first opening 140.

A projection of the axis 148 of the third opening 150 onto the anchor plane 182 is disposed at a third primary angle of 30 degrees relative to the second surface 126 of the body 110 toward the superior surface 120. A projection of the axis 156 of the fourth opening 154 onto the anchor plane 182 is disposed at a fourth primary angle of 30 degrees relative to the second surface 126 of the body 110 and transverse to the projection of the axis 152 of the third opening 150 onto the anchor plane 182.

A projection of the axis 162 of the fifth opening 160 onto the anchor plane 182 is disposed at a fifth primary angle of 30 degrees relative to the second surface 126 of the body 110 toward the superior surface 120. A projection of the axis 166 of the sixth opening 164 onto the anchor plane 182 is disposed at a sixth primary angle of 30 degrees relative to the second surface 126 of the body 110 and transverse to the projection of the axis 162 of the fifth opening 160 onto the anchor plane 182.

The third opening 150, fourth opening 154, fifth opening 160, and sixth openings 164 are also angled inwardly toward the anchor plane 182. The axis 152 of the third opening 150 intersects the anchor plane 182 at a third secondary angle of 15 degrees, and the axis 156 of the fourth opening 154 intersects the anchor plane 182 at a fourth secondary angle of 15 degrees. The axes of the third opening 150 and the fourth opening 154 intersect the anchor plane 182 at a first point that is closer to the second surface 126 than to the first surface 124 such that the axes of the third opening 150 and the fourth opening 154 are angled inwardly. The axis 162 of the fifth opening 160 intersects the anchor plane 182 at a fifth secondary angle of 15 degrees or less, and the axis of the sixth opening 164 intersects the anchor plane 182 at a sixth secondary angle of 15 degrees. The axes 162, 166 of the fifth opening 160 and the sixth opening 164 intersect the anchor plane 182 at a second point that is closer to the second surface 126 than to the first surface 124 such that the axes of the fifth opening 160 and the sixth opening 164 are angled inwardly.

Although the axes of each of the openings are oriented at specific primary angles in FIGS. 1-5, in some implementations, each of the first, second, third, fourth, fifth, and sixth primary angles are any angle from 15 degrees to 60 degrees.

Although the axes of the third opening 150 and the fourth opening 154 of the implant 100 shown in FIGS. 1-9 intersect the anchor plane 182 at a first point that is closer to the second surface 126 than to the first surface 124, in some implementations, the first point is closer to the first surface 124 than to the second surface 126 such that one or both of the axes of the third opening 150 and the fourth opening 154 are angled outwardly. In some implementations, one or both of the axes of the third opening 150 and the fourth opening 154 extend parallel to the anchor plane 182. Although the axes 162, 166 of the fifth opening 160 and the sixth opening 164 of the implant 100 shown in FIGS. 1-9 intersect the anchor plane 182 at a second point that is closer to the second surface 126 than to the first surface 124, in some implementations, the second point is closer to the first surface 124 than to the second surface 126 such that one or both of the axes of the fifth opening 160 and the sixth opening 164 are angled outwardly. In some implementations, one or both of the axes 162, 166 of the fifth opening 160 and the sixth opening 164 extend parallel to the anchor plane 182.

Although the body 110 of the implant 100 shown in FIGS. 1-9 defines six openings, in some implementations, the implant 100 has any number of two or more openings. For example, an implant 200 is shown in the implementation shown in FIGS. 6-9, where the plurality of openings defined by the body 210 further includes a seventh opening 270 and an eighth opening 274. Like the first opening 240 and the second opening 244, the seventh opening 270 and the eighth opening 274 at least partially overlap at the first surface 224 and are configured such that a first anchor 299 is disposable within the seventh opening 270 and a second anchor 299 is disposable within the eighth opening 274 simultaneously.

The axis 272 of the seventh opening 270 is transverse to the axis 276 of the eighth opening 274, and the axes of the seventh opening 270 and eighth opening 274 extend parallel to the anchor plane 282. The axis 272 of the seventh opening 270 is disposed at a 45 degree angle relative to the second surface 226 of the body 210, and the axis 276 of the eighth opening 274 is disposed at a 45 degree angle relative to the second surface 126 of the body 210. But in other implementations, the seventh opening 270 and the eighth opening 274 can be disposed an any angle between 15 and 60 degrees relative to the second surface 126 of the body 210. And, the eighth opening 274 can be disposed at any angle relative to the axis 272 of the seventh opening 270.

Although anchors 199, 299 shown in FIGS. 1-9 are inserted through the first surface 124, 224 and the second surface 126, in some implementations, any portion of the outer surface of the body defines anchor openings for receiving screws or other types of anchors and the openings extend to the opposite portion of the inner surface.

In the implementation shown in FIGS. 1-3 and 6-8, the openings of the device are configured to accept bi-directional bone screws 199, 299. But, in other implementations, the openings are configured to accept single direction screws, blades, or any other fastener or anchor suitable to couple an implant to a spinal column.

Figure 2:
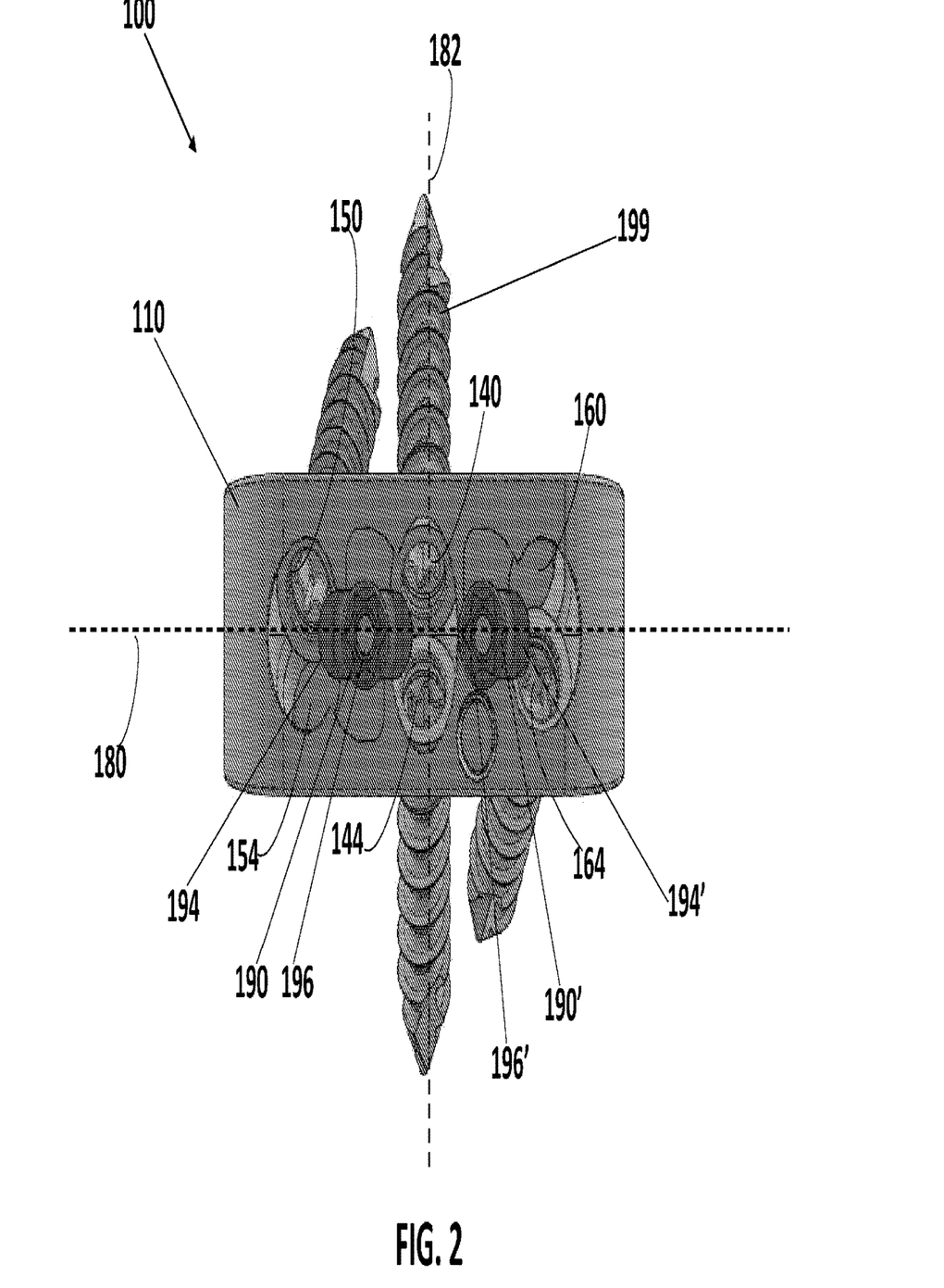
FIG. 2 is a front view of the implant of FIG. 1.
Figure 3:
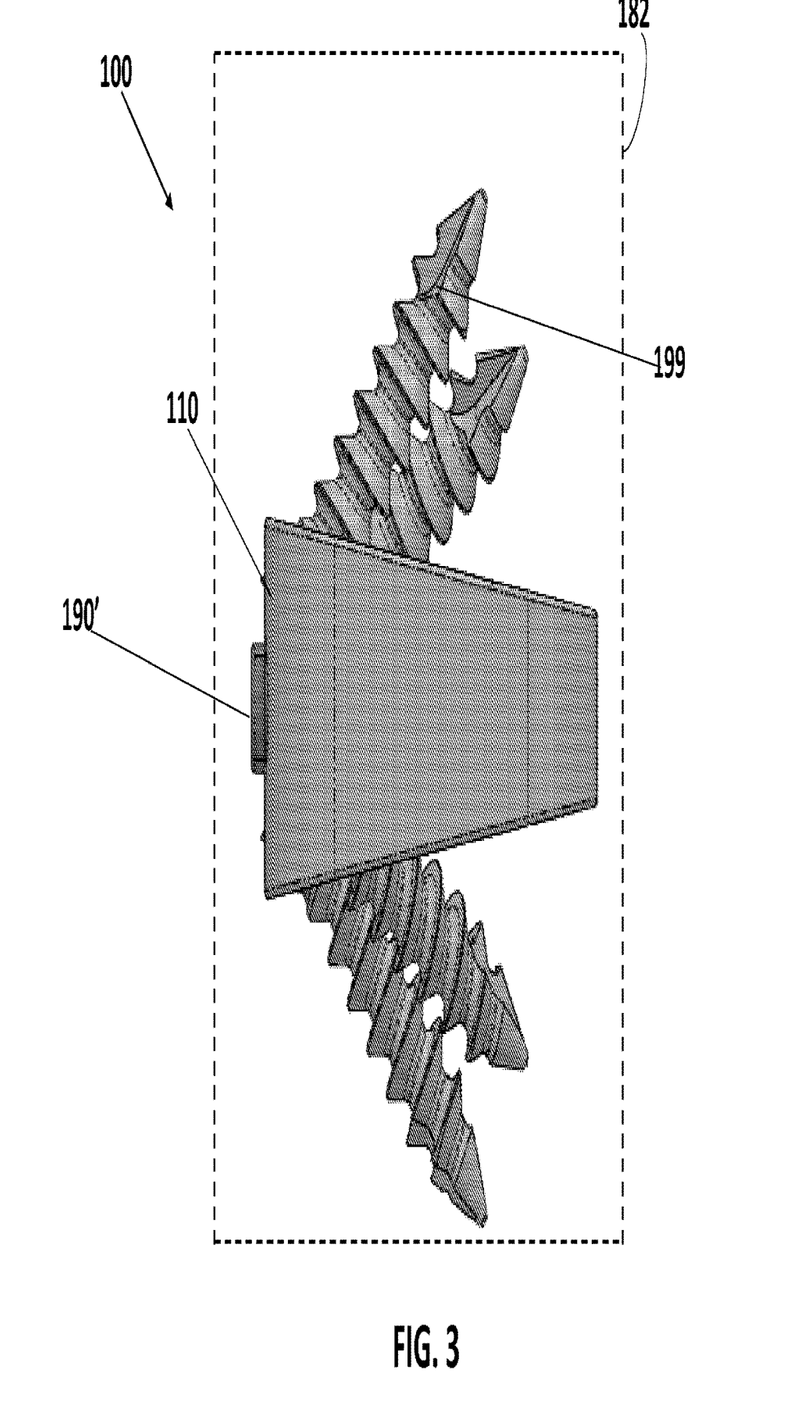
FIG. 3 is a side view of the implant of FIG. 1.
Figure 4:
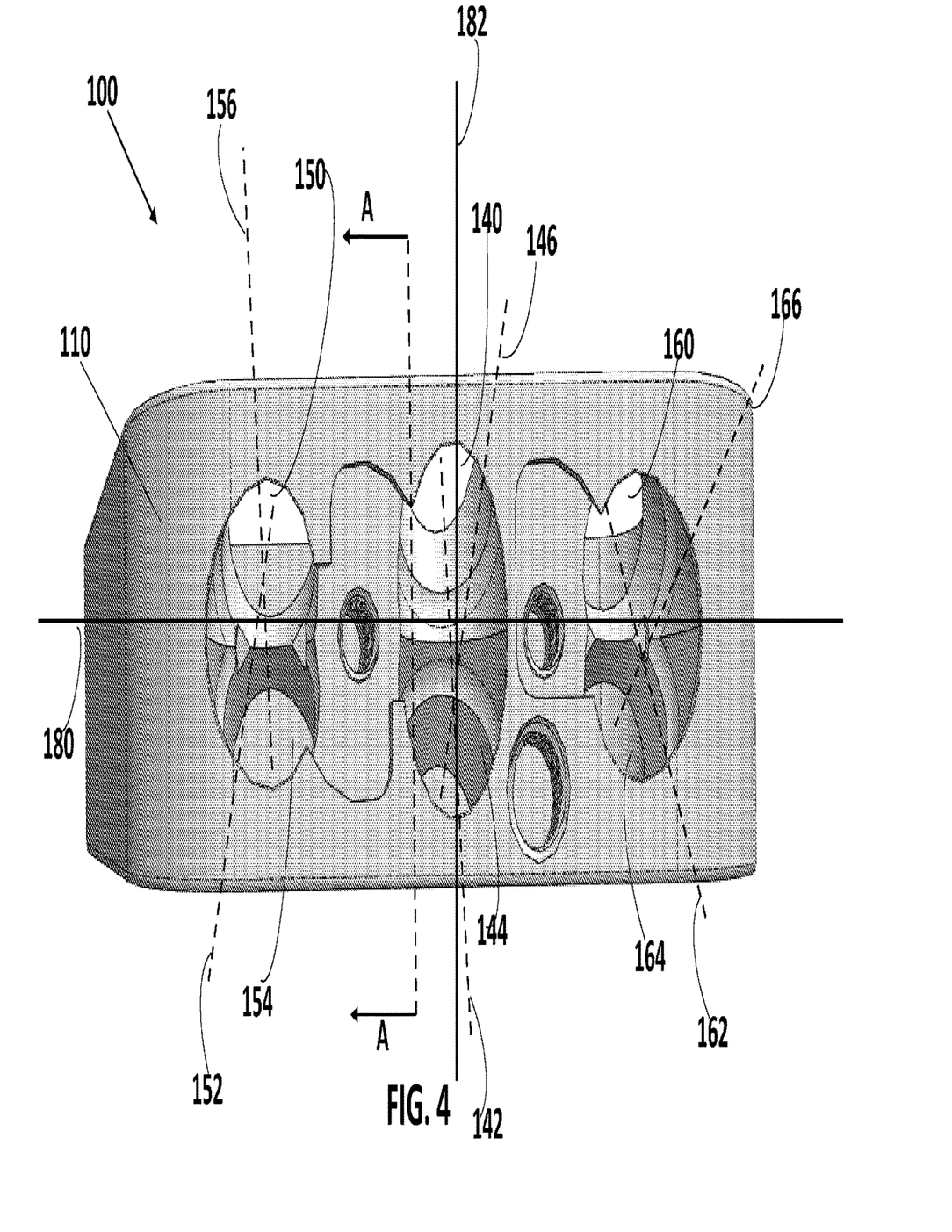
FIG. 4 is a front perspective view of the implant of FIG. 1 without screws
Figure 5:
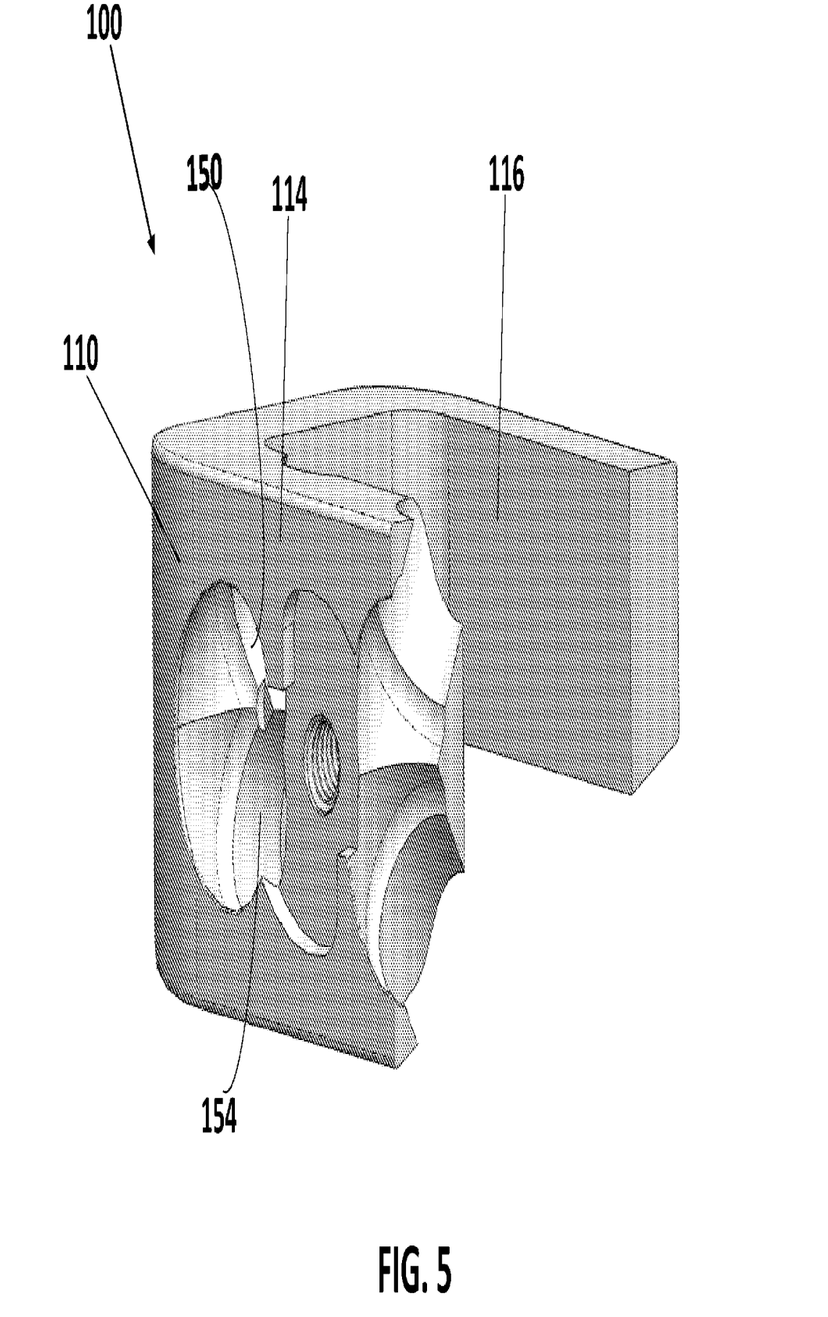
FIG. 5 is a cross-sectional view of the implant of FIG. 1 along line A-A.
Figure 6:
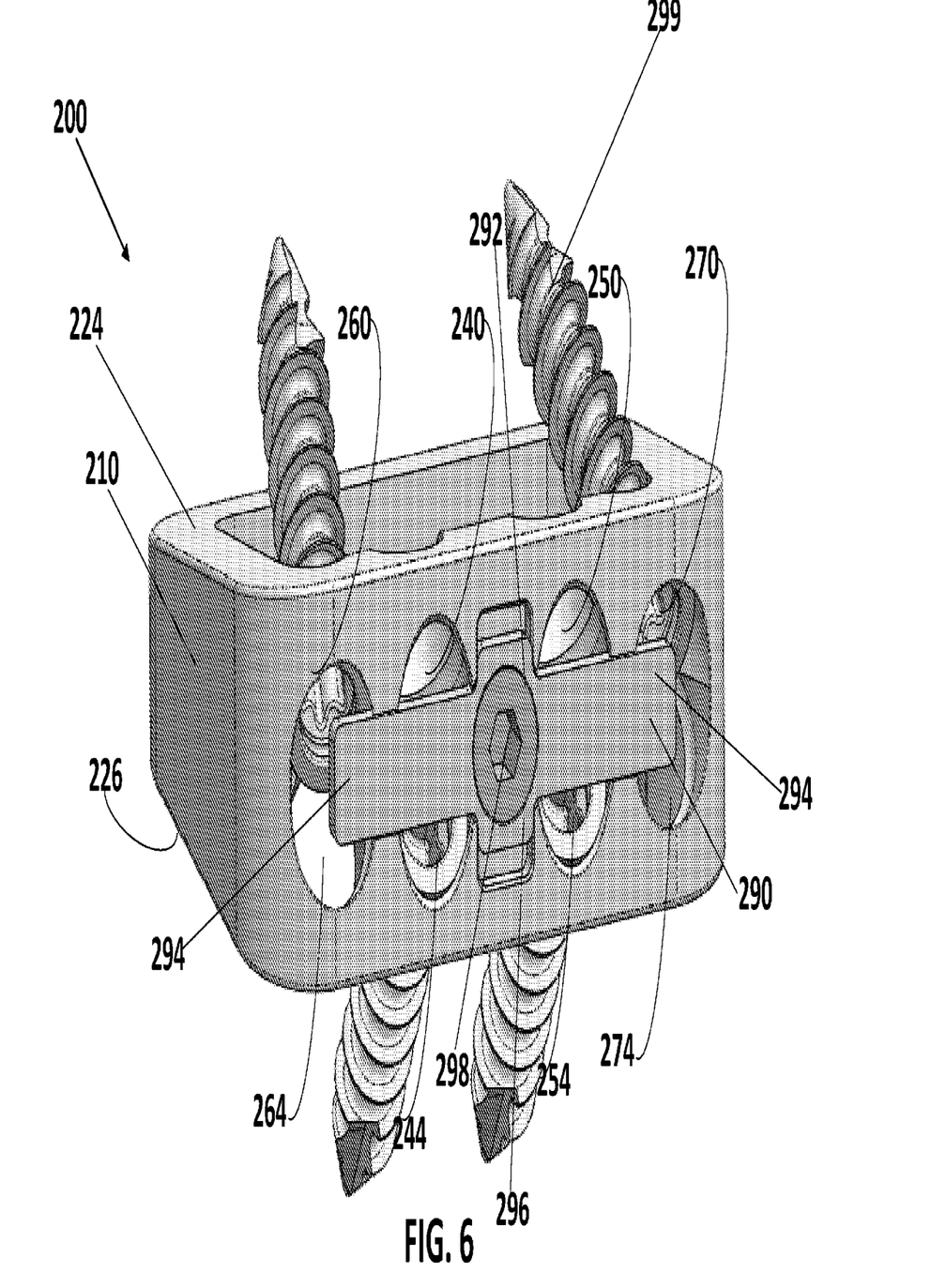
FIG. 6 is a front perspective view of an implant, according to another implementation.
Figure 7:
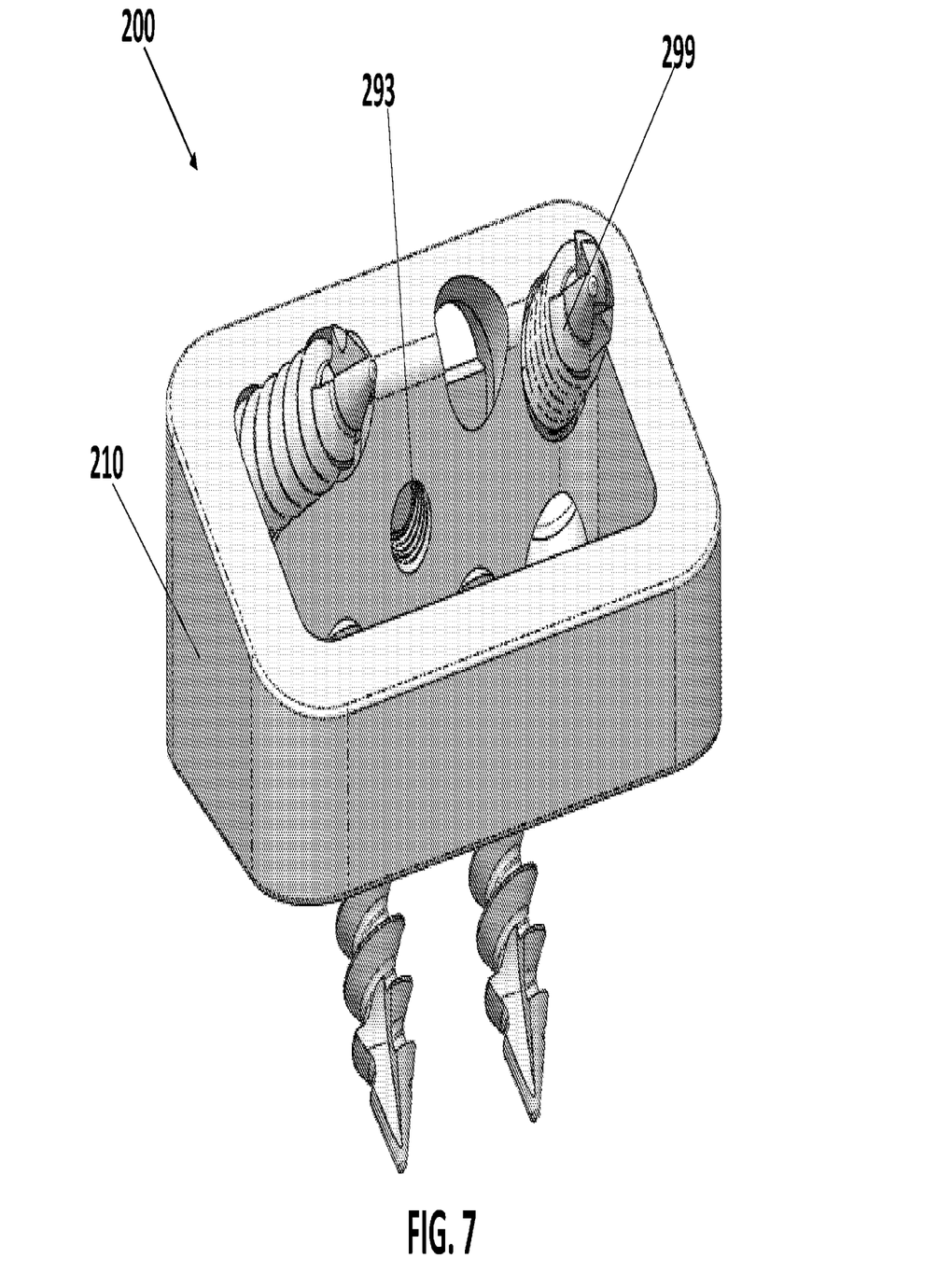
FIG. 7 is a rear perspective view of the implant of FIG. 6.
Figure 8:
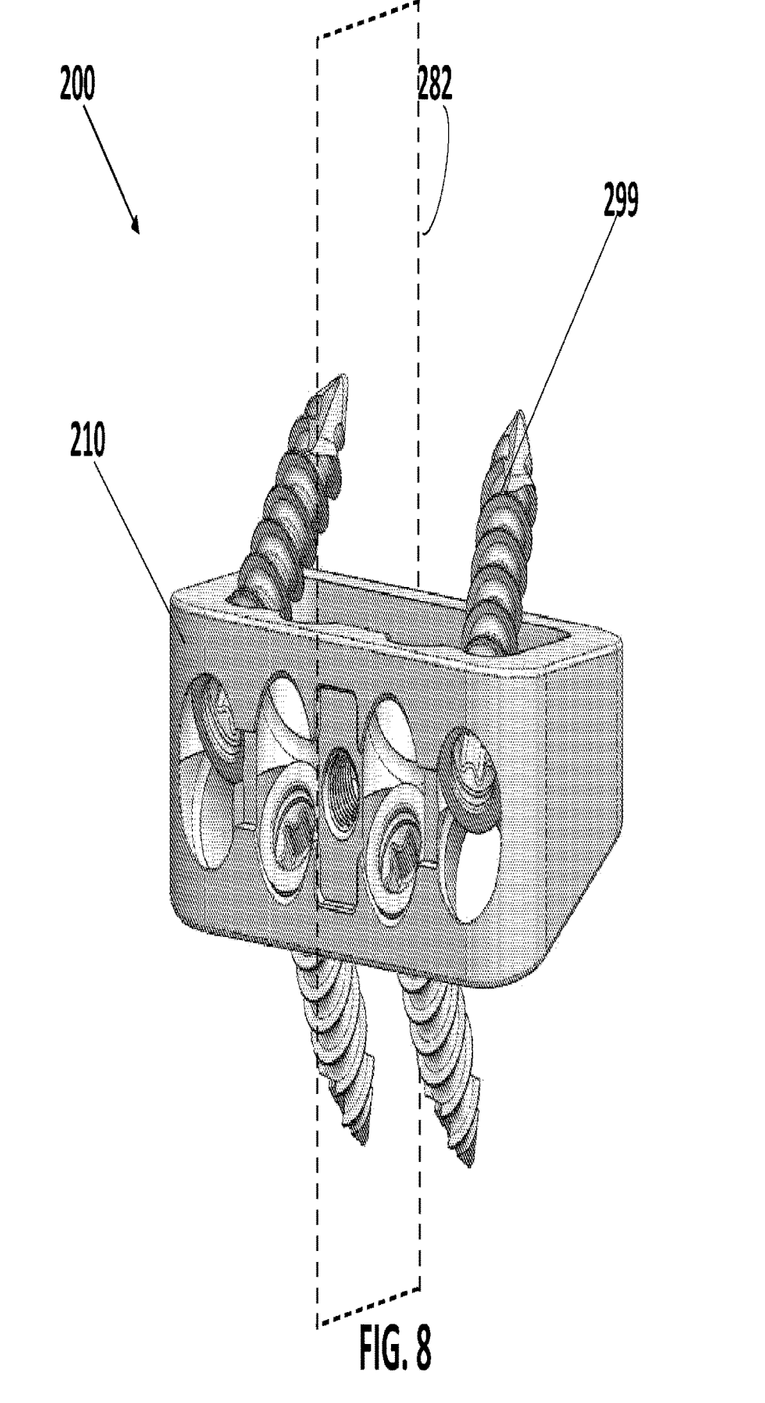
FIG. 8 is a front perspective view of the implant of FIG. 6 with the anti-backout device removed.
Figure 9:
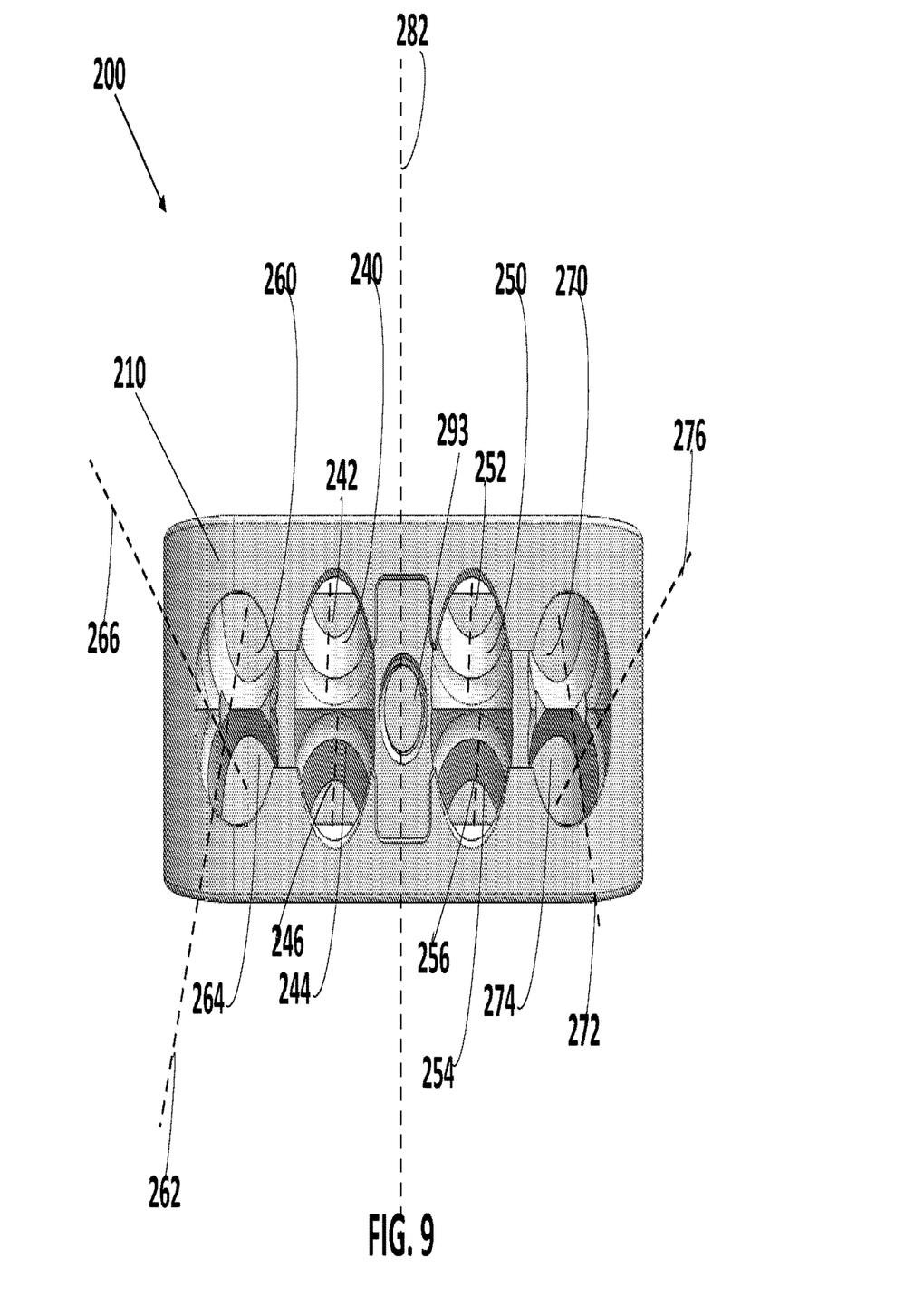
FIG. 9 is a front view of the implant of FIG. 6 without screws.

FIGS. 1-3 show that a first anchor 199 is disposable within the first opening 140, and a second anchor 199 is disposable within the second opening, simultaneously. FIGS. 6-8 show that a third anchor 199 is disposable within the seventh opening 270, and a fourth anchor 199 is disposable within the eighth opening 274, simultaneously. Because of the spacing of the third opening 150 and the fourth opening 154, and the spacing of the fifth opening 160 and the sixth opening 164, only one anchor 199 is disposable within one of the third opening 150 and the fourth opening 154 at a time, and only one anchor 199 is disposable within one of the fifth opening 160 and the sixth opening 164 at a time. However, in other implementations, the third and fourth openings 150, 154 are configured to each receive an anchor 199 simultaneously, the fourth and fifth openings 154, 160 are configured to each receive an anchor 199 simultaneously, or both.

FIGS. 1-3 show an implementation that includes a first anti-backout device 190 and a second anti-backout device 190' coupled to the first surface 124 of the body. The anti-backout devices are positionable to cover a portion of at least the first opening 140, the second opening, the third opening 150, and the fourth opening 154. The second anti-backout device is positionable cover to a portion of the fifth opening 160 and the sixth opening 164. The anti-backout devices 190, 190' each have an anti-backout body 196, 196'. The first anti-backout device 190 has two locking tabs 194 extending radially from the anti-backout body 196. The second anti-backout device 190' has one locking tab 194' extending radially from the anti-backout body 196'. The anti-backout bodies 196, 196' are rotatably coupled to the first surface 124, and the anti-backout devices 190, 190' are rotatable relative to the first surface 124 from a first position (not shown) to a second position (shown in FIGS. 1-3). The locking tabs 194, 194' are structured such that, when the anti-backout devices 190, 190' are in the first position, none of the locking tabs 194, 194' are covering any portion of the first, second, third, fourth, fifth, or sixth openings 140, 144, 150, 154, 160, 164. After each anti-backout device 190, 190' has been rotated from the first position to the second position, each of the locking tabs 194, 194' is at least partially covering one of the six openings 140, 144, 150 154, 160, 164 such that the locking tabs 194, 194' are in a position to prevent the fasteners 150 disposed in each of the openings 130, 140, 144, 150 154, 160, 164 from coming out of the fastener's 150 respective opening 130, 140, 144, 150 154, 160, 164 (also called "backing out").

FIGS. 6-7 show another implementation of an anti-backout device 290 coupled to the first surface 124 of the body 210. The anti-backout device 290 is positioned onto the first surface 224 such that the anti-backout device 290 at least partially overlaps with each of the eight openings 240, 244, 250 254, 260, 264. The anti-backout device 290 has an anti-backout body 296 and two locking tabs 294 extending radially from the body 292. The anti-backout device defines a first fastening hole 292, and the first surface 224 of the body defines a second fastening hole 293. A screw 299 extends through the first opening 240 and the second opening 244 to couple the anti-backout device to the first surface 224. When the anti-backout device is coupled to the first surface 224 of the body 210, each of the locking tabs 294 is at least partially covering each of the eight openings 240, 244, 250, 254, 260, 264 270, 274 such that the locking tabs 294 are in a position to prevent the fasteners 150 disposed in each of the eight fastener openings 240, 244, 250, 254, 260, 264, 270, 274 from backing out.

During an implanting procedure, the surgeon selects an implant 100 with a specific lordosis angle to compliment the curvature of the patient's spine where the implant will be inserted. The implant 100 is inserted between two adjacent lumbar vertebrae (L1-S1) from anterior to posterior of the patient such that the second surface 126 faces toward the posterior of the patient and the superior surface 120 faces the head of the patient.

Once the implant 100 is disposed between the adjacent vertebrae, screws 199 are inserted through the openings of the implant 100 and secured into selected sections of the spine. A surgeon observing the spine of the patient identifies any existing hardware or conditions in the patient's spine and determines which openings of the implant 100 to use for coupling the implant 100 to the vertebrae. The multiple openings extending at various angles provides the surgeon with multiple options for anchor points in the spine. At least a first anchor 199 is inserted through one of the first, third, or fifth opening 160 s to couple the implant 100 to the superior vertebrae, and at least a second anchor 199 is inserted through one of the second, fourth, or sixth openings 144, 154, 164 to couple the implant 100 to the inferior vertebrae. Third and fourth anchors 199 can be inserted into the remaining openings to further secure the implant 100 to the superior and inferior vertebrae. The screws 199 are advanced into the spine until the screw heads no longer protrude from the first surface 124.

The anti-backout device(s) are secured into place to prevent the screws 199 from backing out. The anti-backout devices shown in FIGS. 1-3 are secured by rotating the anti-backout devices such that a portion of each kicking tab 194 194' overlaps with each of the openings. If a device including the anti-backout device shown in FIGS. 6-7 is being used, then the anti-backout device is positioned onto the first surface 224 such that the anti-backout device at least partially overlaps with each of the eight openings. A bolt 298 is then inserted through the fastening hole 292 in the anti-backout device 290 and into a second fastener opening 293 in the body 210 of the implant 100 device to couple the anti-backout device to the body 210.

A number of implementations have been described. Nevertheless, it will be understood that various modifications may be made without departing from the spirit and scope of the claims. Accordingly, other implementations are within the scope of the following claims.

Certain terminology is used herein for convenience only and is not to be taken as a limitation on the present claims. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. An implant comprising a body defining a central opening; said body has a first surface and a second surface spaced apart and opposite from the first surface; said second surface at least partially defines said central opening; said first surface defines a plurality of openings including a first opening, a second opening, a third opening, a fourth opening, a fifth opening and a sixth opening; each of said openings extends along an axis from said first surface to said second surface; said first opening and said second opening at least partially overlap at said first surface; said axis of said first opening is non-parallel to said axis of said second opening; said third opening and said fourth opening at least partially overlap at said first surface; said axis of said third opening is non-parallel to said axis of said fourth opening; said fifth opening and said sixth opening at least partially overlap at said first surface; said axis of said fifth opening is non-parallel to said axis of said sixth opening.

2. The implant as defined in claim 1, wherein said axis of said first opening is transverse to said axis of said second opening.

3. The implant as defined in claim 2, wherein said axis of said third opening is transverse to said axis of said fourth opening.

4. The implant as defined in claim 2, wherein said axis of said fifth opening is transverse to said axis of said sixth opening.

5. The implant as defined in claim 4, wherein said first surface of said body further includes an alignment axis; an intersection point of said axis of said first opening with said first surface and an intersection point of said axis of said second opening with said first surface are equally spaced on opposite sides of said alignment axis from each other; an intersection point of said axis of said third opening with said first surface and an intersection point of said axis of said fourth opening with said first surface are equally spaced on opposite sides of said alignment axis from each other.

6. The implant as defined in claim 5, further comprising an anti-backout device coupled to said first surface of said body; said anti-backout device is configured to be positionable to cover a portion of at least one of said first, second, third or fourth openings.

7. The implant as defined in claim 6, wherein said implant comprises an interbody device.

8. The implant as defined in claim 7, wherein said body is at least partially formed of one or more materials selected from the group consisting of molybdenum-rhenium (MoRe) alloy, titanium-molybdenum (TiMo) alloy, titanium (Ti) alloy, and polyether ether ketone ("PEEK").

9. The implant as defined in claim 8, wherein said body includes a plurality of micro-apertures and a plurality of macro-apertures; each of said micro-apertures has an average size of 2-10 micrometers (μm); each of said macro-apertures has an average size of 300-800 micrometers (μm).

10. The implant as defined in claim 1, wherein said axis of said third opening is transverse to said axis of said fourth opening.

11. The implant as defined in claim 1, wherein said axis of said fifth opening is transverse to said axis of said sixth opening.

12. The implant as defined in claim 1, wherein said first surface of said body further includes an alignment axis; an intersection point of said axis of said first opening with said first surface and an intersection point of said axis of said second opening with said first surface are equally spaced on opposite sides of said alignment axis from each other; an intersection point of said axis of said third opening with said first surface and an intersection point of said axis of said fourth opening with said first surface are equally spaced on opposite sides of said alignment axis from each other.

13. The implant as defined in claim 1, further comprising an anti-backout device coupled to said first surface of said body; said anti-backout device is configured to be positionable to cover a portion of at least one of said first, second, third or fourth openings.

14. The implant as defined in claim 1, wherein said implant comprises an interbody device.

15. The implant as defined in claim 1, wherein said body is at least partially formed of one or more materials selected from the group consisting of molybdenum-rhenium (MoRe) alloy, titanium-molybdenum (TiMo) alloy, titanium (Ti) alloy, and polyether ether ketone ("PEEK").

16. The implant as defined in claim 1, wherein said body includes a plurality of micro-apertures and a plurality of macro-apertures; each of said micro-apertures has an average size of 2-10 micrometers (um); each of said macro-apertures has an average size of 300-800 micrometers (um).

17. An interbody device comprising a body defining a central opening; said body having a first surface and a second surface spaced apart and opposite from said first surface; said first surface includes first, second third and fourth sides; said second surface at least partially defines said central opening; said first side of said first surface includes a first opening, a second opening, a third opening, a fourth opening, a fifth opening and a sixth opening; each of said first, second, third, fourth, fifth and sixth openings extends along an axis from said first surface to said second surface; said first opening and said second opening at least partially overlap at said first surface; said axis of said first opening is non-parallel to said axis of said second opening; said third opening and the fourth opening at least partially overlap at said first surface; said axis of said third opening is non-parallel to said axis of said fourth opening; said first surface of said body further includes an alignment axis; an intersection point of said axis of said first opening with said first surface and an intersection point of said axis of said second opening with said first surface are equally spaced on opposite sides of said alignment axis from each other; an intersection point of said axis of said third opening with said first surface and an intersection point of said axis of said fourth opening with said first surface are equally spaced on opposite sides of said alignment axis from each; said fifth opening and said sixth opening at least partially overlap at said first surface; said axis of said fifth opening is non-parallel to said axis of said sixth opening.

18. The interbody device as defined in claim 17, wherein said axis of said first opening is transverse to said axis of said second opening.

19. The interbody device as defined in claim 18, wherein said axis of said third opening is transverse to said axis of said fourth opening.

20. The interbody device as defined in claim 19, wherein said axis of said fifth opening is transverse to said axis of said sixth opening.

21. The interbody device as defined in claim 20, wherein an intersection point of said axis of said fifth opening with said first surface and an intersection point of said axis of said sixth opening with said first surface are equally spaced on opposite sides of said alignment axis from each other.

22. The interbody device as defined in claim 21, further comprising an anti-backout device coupled to said first surface of said body; said anti-backout device is configured to be positionable to cover a portion of at least one of said first, second, third or fourth openings.

23. The interbody device as defined in claim 22, wherein said body is at least partially formed of one or more materials selected from the group consisting of molybdenum-rhenium (MoRe) alloy, titanium-molybdenum (TiMo) alloy, titanium (Ti) alloy, and polyether ether ketone ("PEEK").

24. The interbody device as defined in claim 23, wherein said body includes a plurality of micro-apertures and a plurality of macro-apertures; each of said micro-apertures has an average size of 2-10 micrometers (μm); each of said macro-apertures has an average size of 300-800 micrometers (μm).

25. The interbody device as defined in claim 17, wherein said axis of said third opening is transverse to said axis of said fourth opening.

26. The interbody device as defined in claim 17, wherein said axis of said fifth opening is transverse to said axis of said sixth opening.

27. The interbody device as defined in claim 26, wherein an intersection point of said axis of said fifth opening with said first surface and an intersection point of said axis of said sixth opening with said first surface are equally spaced on opposite sides of said alignment axis from each other.

28. The interbody device as defined in claim 17, further comprising an anti-backout device coupled to said first surface of said body; said anti-backout device is configured to be positionable to cover a portion of at least one of said first, second, third or fourth openings.

29. The interbody device as defined in claim 17, wherein said body is at least partially formed of one or more materials selected from the group consisting of molybdenum-rhenium (MoRe) alloy, titanium-molybdenum (TiMo) alloy, titanium (Ti) alloy, and polyether ether ketone ("PEEK").

30. The interbody device as defined in claim 17, wherein said body includes a plurality of micro-apertures and a plurality of macro-apertures; each of said micro-apertures has an average size of 2-10 micrometers (tum); each of said macro-apertures has an average size of 300-800 micrometers (um).

* * * * *